(12) United States Patent
Austin et al.

(10) Patent No.: US 11,266,440 B2
(45) Date of Patent: Mar. 8, 2022

(54) TOOLS AND METHOD FOR SUBCUTANEOUS DEVICE INSERTION

(71) Applicant: BIOTRONIK SE & CO. KG, Berlin (DE)

(72) Inventors: Eric Austin, Portland, OR (US); Hannes Kraetschmer, West Linn, OR (US); Stevan Wittenbrock, Portland, OR (US); Daniel R. Baker, Seattle, WA (US); Christopher J. Jensen, Beaverton, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 427 days.

(21) Appl. No.: 15/938,169

(22) Filed: Mar. 28, 2018

(65) Prior Publication Data

US 2018/0280056 A1 Oct. 4, 2018

Related U.S. Application Data

(60) Provisional application No. 62/478,618, filed on Mar. 30, 2017.

(51) Int. Cl.
*A61B 17/34* (2006.01)
*A61B 5/283* (2021.01)
*A61B 17/32* (2006.01)

(52) U.S. Cl.
CPC .......... *A61B 17/3468* (2013.01); *A61B 5/283* (2021.01); *A61B 2017/320056* (2013.01); *A61B 2560/063* (2013.01)

(58) Field of Classification Search
CPC ...... A61N 1/05; A61N 1/0502; A61N 1/0504; A61F 9/0008; A61F 9/0017; A61F 9/0026; A61F 2/9661; A61F 2/9662; A61F 2002/9665; A61B 17/3468; A61B 5/042; A61B 2017/320056; A61B 2560/063;

(Continued)

(56) References Cited

U.S. PATENT DOCUMENTS 4,428,370 A * 1/1984 Keely ....................... A61F 6/12
128/838
5,304,119 A 4/1994 Balaban et al.
(Continued)

FOREIGN PATENT DOCUMENTS

GB 632812 A 12/1949
WO 2017035038 A1 3/2017

OTHER PUBLICATIONS

Merriam-Webster definition of "define" https://www.merriam-webster.com/dictionary/define, accessed Jun. 30, 2021, copyright 2021 (Year: 2021).*

*Primary Examiner* — Wade Miles
*Assistant Examiner* — Kankindi Rwego
(74) *Attorney, Agent, or Firm* — Laurence A. Greenberg; Werner H. Stemer; Ralph E. Locher

(57) ABSTRACT

An implantation tool for implanting a medical device subcutaneously includes a core extending along a longitudinal axis. The core is formed with a longitudinal recess extending along the longitudinal axis. A shell protrudes from an end of the core in the direction of the longitudinal axis. The shell defines a compartment for carrying the medical implant. The compartment is connected to the longitudinal recess. A rod that extends along the longitudinal axis is arranged in the longitudinal recess.

18 Claims, 13 Drawing Sheets

(58) Field of Classification Search
CPC ............ A61B 2017/347; A61B 5/0421; A61B 5/0422; A61B 2560/066
USPC ........................................................ 606/129
See application file for complete search history.

(56) References Cited

U.S. PATENT DOCUMENTS

| | | |
|---|---|---|
| 5,507,807 A | 4/1996 | Shippert |
| 6,488,649 B1* | 12/2002 | Lichten .............. A61B 17/3468 221/303 |
| 6,530,896 B1 | 3/2003 | Elliott |
| 2003/0208153 A1* | 11/2003 | Stenzel .............. A61B 17/3468 604/60 |
| 2003/0233126 A1* | 12/2003 | Kaplan .................... A61N 1/08 607/3 |
| 2010/0094252 A1 | 4/2010 | Wengreen et al. |
| 2010/0331868 A1 | 12/2010 | Bardy |
| 2014/0276928 A1 | 9/2014 | Vanderpool et al. |
| 2015/0045805 A1* | 2/2015 | Kontur .................. A61F 2/1678 606/107 |
| 2015/0257787 A1 | 9/2015 | Haigh et al. |
| 2016/0175007 A1 | 6/2016 | Valbuena et al. |
| 2017/0049467 A1 | 2/2017 | Foster et al. |

* cited by examiner

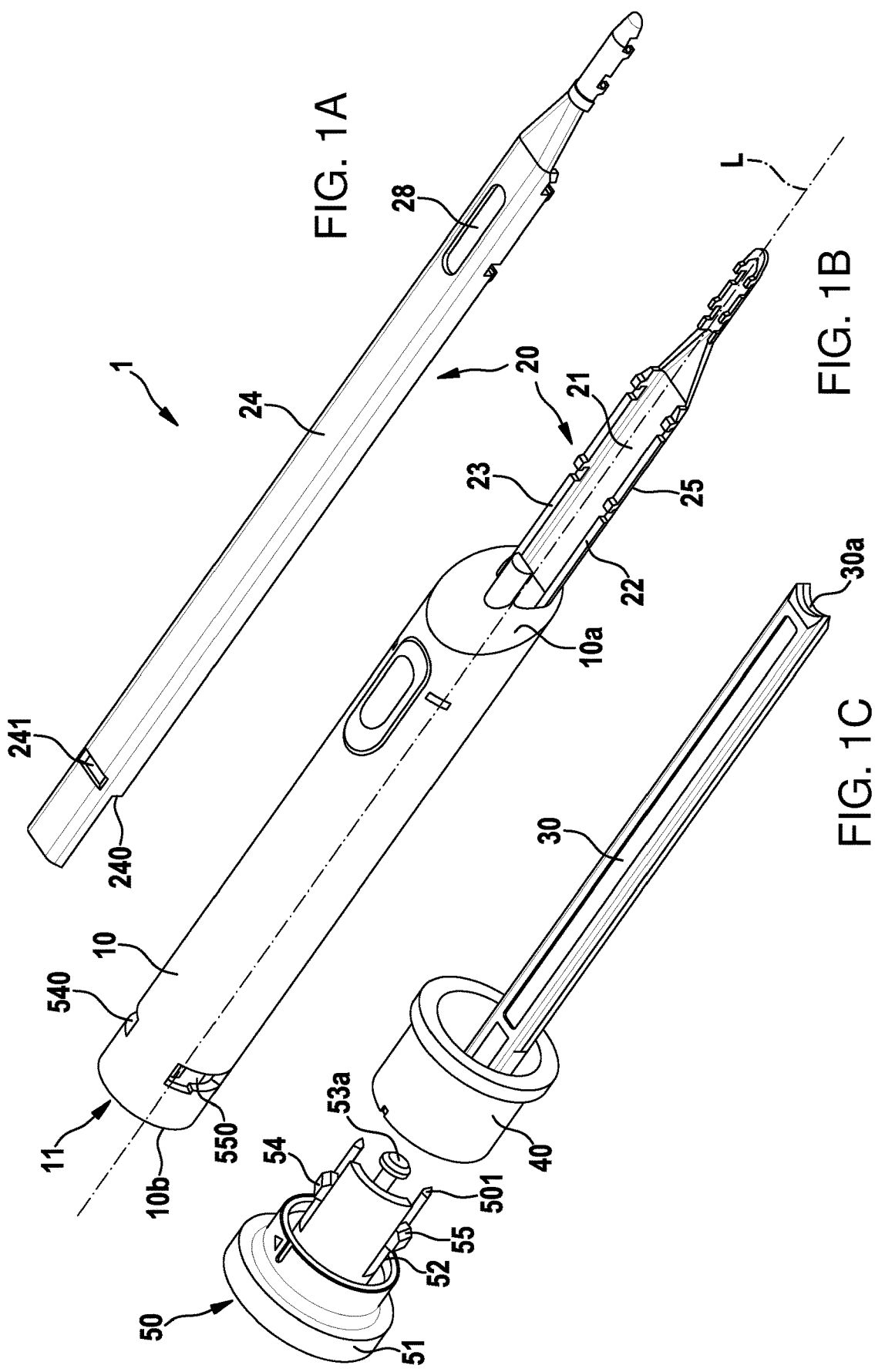

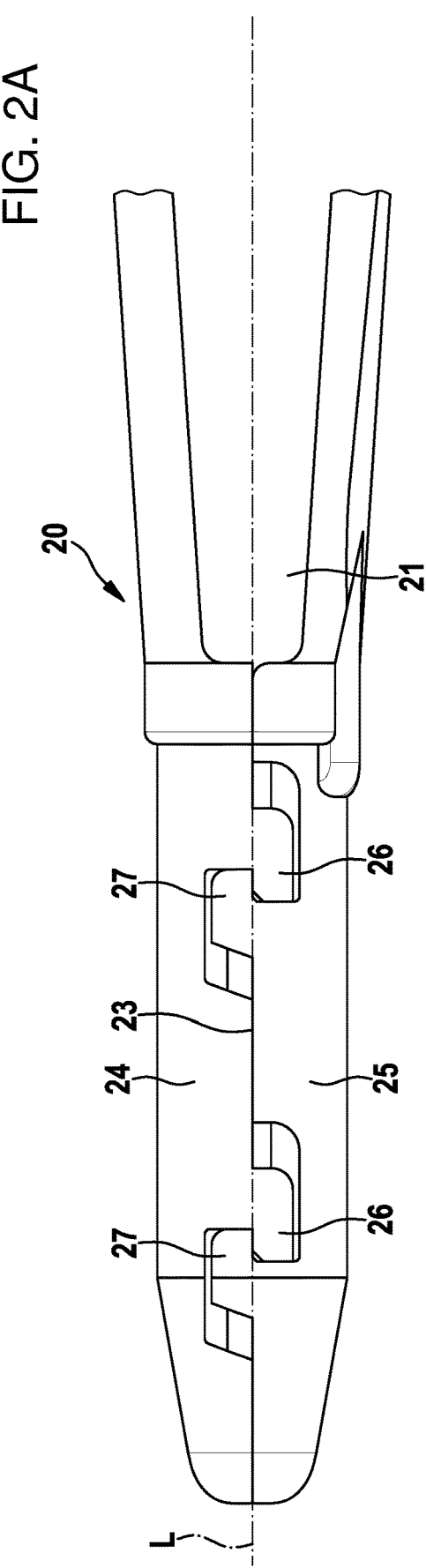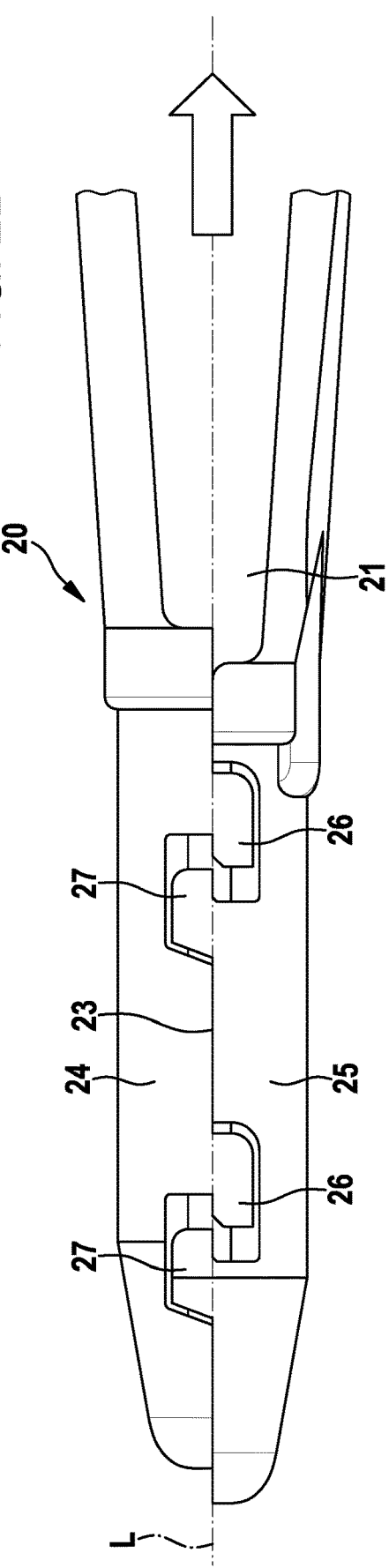

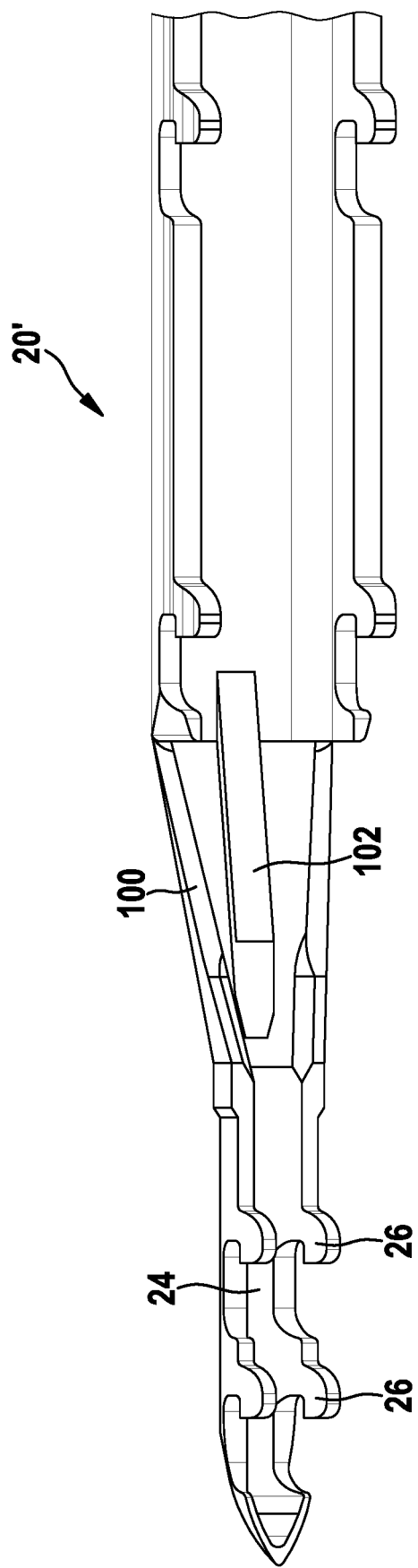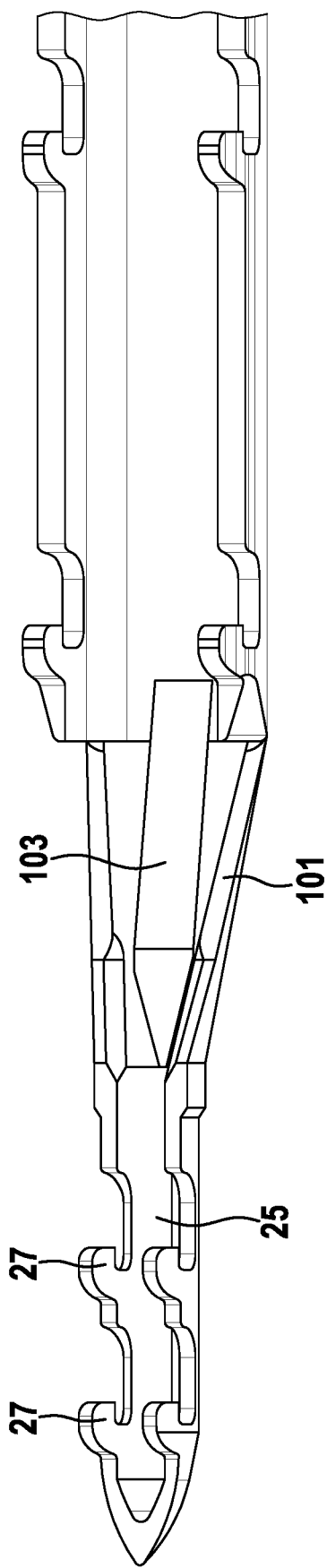

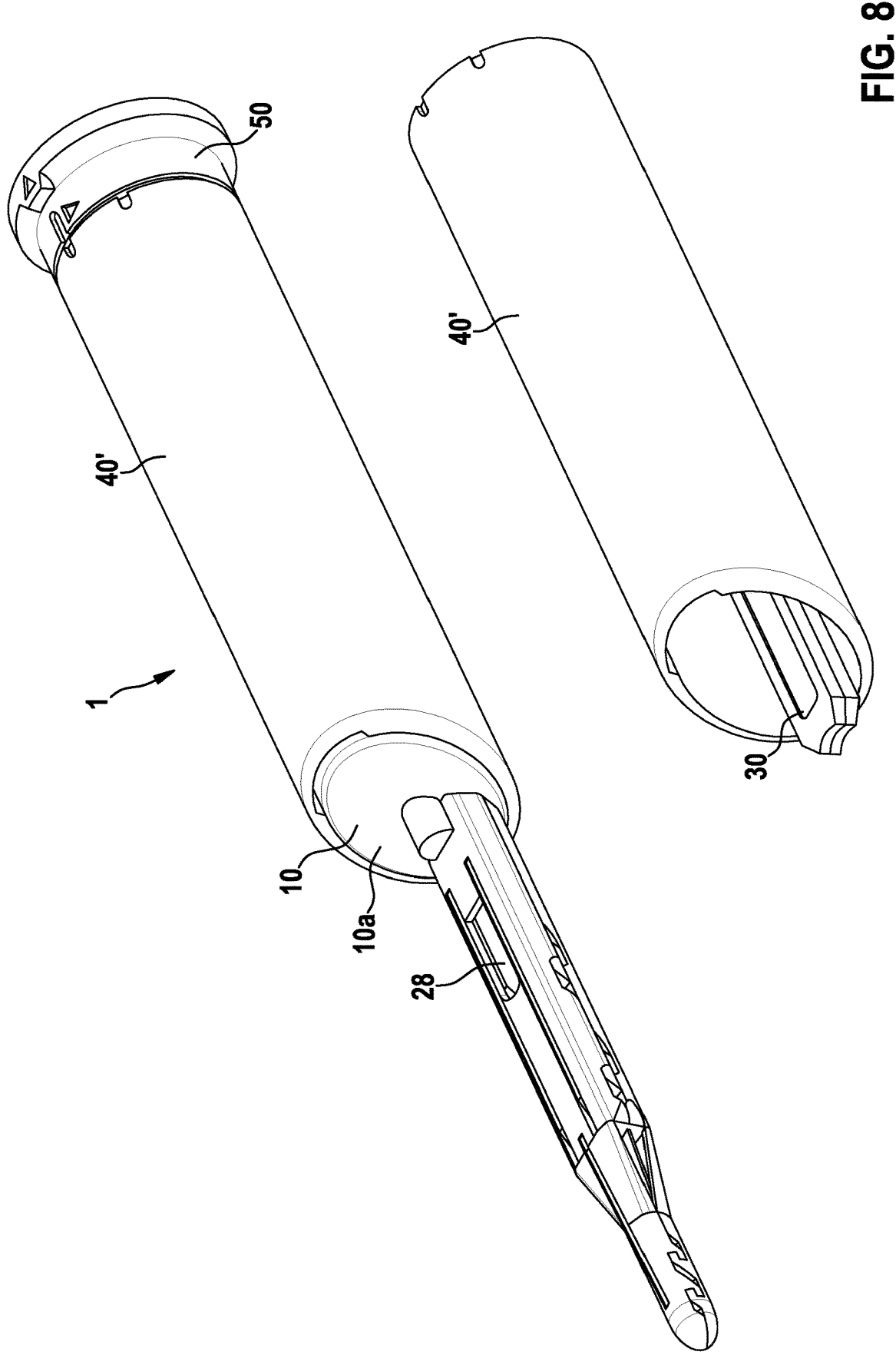

TOOLS AND METHOD FOR SUBCUTANEOUS DEVICE INSERTION

CROSS-REFERENCE TO RELATED APPLICATION

This application claims the priority, under 35 U.S.C. § 119(e), of provisional patent application No. 62/478,618 filed Mar. 30, 2017; the prior application is herewith incorporated by reference in its entirety.

BACKGROUND OF THE INVENTION

Field of the Invention

The invention relates to an implantation tool for implanting a medical device, particularly an implantable cardiac monitoring device subcutaneously.

Such an implantable cardiac monitoring device is configured to monitor signals from the heart of the patient, particularly ECG signals in order to be able to, say, assess the condition of the heart, particularly heart failure (HF) and cardiac vascular diseases (CVD).

Regarding such devices, surgical tools have been developed that emphasize the "injectability" of such devices by employing syringe-like features (e.g., plungers), in order to achieve a relatively fast implantation procedure, minimizing surgical time and patient discomfort.

Published patent application US 2010/0094252 A1 discloses an implantation tool to which a tunneler is attached. The medical device is situated in the tunneler.

U.S. Pat. No. 6,530,896 B1 and published patent application US 2015/0257787 A1 both disclose distal tip caps, which are removable, biodegradable and/or slitable.

Published patent application US 2014/0276928 A1 also discloses an implantation tool using a tunneler and a plunger.

Finally, published patent application US 2016/0175007 A1 discloses systems and methods for implanting an implantable cardiac monitor.

BRIEF SUMMARY OF THE INVENTION

Based on the above, it is an object of the present invention to provide an implantation tool that allows a fast and easy implantation of a medical device, particularly an implantable cardiac monitoring device.

With the above and other objects in view there is provided, in accordance with the invention, an implantation tool for the subcutaneous implantation of a medical device. The implantation tool comprising:
- a core extending along a longitudinal axis, said core being formed with a longitudinal recess extending along said longitudinal axis;
- a shell protruding from an end of said core in a direction of said longitudinal axis, said shell defining a compartment, connected to said longitudinal recess, for carrying the medical implant, and said shell having a locked configuration and an unlocked configuration for releasing the medical implant from said shell; and
- a rod extending along the longitudinal axis and arranged in said longitudinal recess, wherein said longitudinal recess is configured such that said rod is in contact with the medical implant when the medical implant is disposed in said core.

In other words, the implantation tool for implanting a medical device subcutaneously includes:
- a core extending along a longitudinal axis, the core comprising a longitudinal recess extending along said longitudinal axis,
- a shell protruding from an end of the core in the direction of the longitudinal axis wherein the shell defines a compartment for carrying the medical implant, which compartment communicates with the longitudinal recess, wherein particularly said shell is configured to be slid through an incision in the skin of the person into the tissue of the person to define a pocket in the tissue under the skin for receiving the medical implant, and wherein the shell comprises at least a locked configuration and an unlocked configuration for releasing the medical implant from the shell, and
- a rod extending along the longitudinal axis and arranged in said longitudinal recess, wherein the arrangement in the longitudinal recess is such that the rod is in contact with the medical implant.

According to an embodiment of the device according to the present invention, for releasing the medical implant from the shell, the core is configured to be moved relative to said rod along the longitudinal axis, whereby the rod slides into said compartment for maintaining contact with the medical implant, whereby the medical implant is kept in one position in relation to the longitudinal axis by said rod, and whereby the medical implant is released from the compartment of the shell (and is thereby arranged in said pocket). The movement of the core relative to the rod leads to a gradual retraction of the shell away from the pocket and the incision, whereby the retraction of the shell gradually releases the medical implant. The medical implant remains in the pocket after being completely released or disengaged from the shell. After the shell is completely retracted from the incision, only the rod temporarily stays in contact with the medical implant until the complete implantation tool is being retracted.

According to an embodiment of the device of the present invention, the implantation tool further comprises an operating member for changing the shell from the locked configuration to the unlocked configuration, which is mounted to an end of the core opposite the shell, wherein the operating member is configured to be rotatable from an initial first position into a second position, wherein the shell is in the unlocked configuration when the operating member is in the second position.

According to an embodiment of the device according to the present invention, the shell is formed with at least one slot.

According to an embodiment of the device according to the present invention, the shell comprises a second slot opposing said first slot. Particularly, both slots extend along said longitudinal axis of the device and meet at a tip of the shell.

Thus, according to an embodiment of the device according to the present invention, the two slots divide the shell into a first part (particularly a top part) and a second part (particularly a bottom part). Particularly, when the two parts are moved/deflected from each other in a direction perpendicular to the longitudinal axis, the two parts pivot away from each other and said slots spread so that an opening of the shell is formed through which the medical implant that is initially arranged in said compartment can be released from the compartment/shell.

However, a mechanism is particularly provided, that allows to maintain the two parts in a locked configuration with respect to one another so that the shell remains in a closed state when the shell is inserted into the tissue of the patient. In the locked configuration the two parts are not allowed to be moved/deflected relatively to each other, neither in longitudinal direction, nor in radial direction, in order to prevent an unintended release of the medical device out of the compartment in the shell.

Particularly, according to an embodiment of the device according to the present invention, the first part of the shell is configured to be moved along the longitudinal direction with respect to the second part of the shell to transform said locked configuration of said two parts of the shell, in which the two parts of the shell cannot be moved/deflected away from each other and said slots remain closed, into an unlocked configuration of said two parts of the shell, in which the two parts of the shell can be moved/deflected away from each other (e.g. as described above) and the slots are opened for releasing the medical implant from the shell. The medical implant is released from the compartment of the shell such that the medical implant is kept in one position in relation to the longitudinal axis by said rod, wherein the shell is configured to be retracted from the medical implant.

Further, according to an embodiment of the device according to the present invention, at each of said slots the first part and the second part each comprise at least one latching member, wherein each latching member of the first part of the shell engages with an associated latching member of the second part of the shell when the first and the second part reside in said locked configuration, and wherein the latching members of the first part are disengaged from the latching members of the second part of the shell when the first and the second part of the shell reside in said unlocked configuration. Particularly, in an embodiment, said latching members are formed as hooks, respectively.

Further, according to an alternative embodiment of the device according to the present invention, the at least one slot is a single slot that is arranged on a top side of the shell. Here, in contrast to the embodiment where two opposing slots are present and the shell particularly opens top to bottom, the shell opens on the top side from side to side.

Particularly, in an embodiment, this single slot extends from a window of the shell that is formed into the top side of the shell towards a tip of the shell, wherein the medical implant is visible through said window when the medical implant is arranged in the compartment defined by the shell.

Further, according to an embodiment of the device according to the present invention, said single slot divides a section of said top side of the shell into a first and a second part, wherein at said slot, the first part and the second part each comprise at least one latching member, wherein each latching member of the first part of the shell engages with an associated latching member of the second part of the shell when the first and the second part reside in the locked configuration, in which the two parts of the shell cannot be deflected from each other (side-to-side) and said at least one slot remains closed, and wherein the latching members of the first part are disengaged from the latching members of the second part of the shell when the first and the second part of the shell reside in said unlocked configuration, in which the two parts of the shell can be moved/deflected away from each other so as to open the at least one slot for releasing the medical implant from the shell. The medical implant is released from the shell such that the shell is retracted from the medical implant while the medical implant is kept in a position by the rod. Again, according to an embodiment, said latching members may be formed as hooks, respectively.

Further, according to an embodiment of the device according to the present invention, the rod is connected to a grip member, which grip member encompasses the core, so that the grip member can be held fixed (with respect to a patient) and the core can slide inside the grip member (when the core is retracted) for sliding the rod into said compartment of the shell.

Further, according to an embodiment of the device according to the present invention, the operating member comprises a knob arranged outside said longitudinal recess for manually rotating the operating member from the first into the second position, from which knob a protrusion protrudes along the longitudinal axis from the knob, which protrusion is arranged in said longitudinal recess.

Further, according to an embodiment of the device according to the present invention, when the operating member resided in its first position, the grip member is locked (arrested) by the operating member when the grip member is arranged adjacent said operating member so that the rod cannot be moved with respect to the core/shell, and wherein when the operating member is rotated into its second position, the grip member is unlocked with respect to the core so that the core can slide inside the grip member for sliding the rod into said compartment of the shell.

Further, according to an embodiment of the device according to the present invention, the operating member comprises a pin protruding in a circumferential direction of the core from the protrusion, wherein said pin engages with a slot formed into the grip member when the grip member is arranged adjacent the knob and the operating member is arranged in its first position. Furthermore, particularly, said pin disengages with the slot of the grip member when the operating member is rotated into its second position so that the grip member is unlocked with respect to the core and the core can slide inside the grip member for sliding the rod into said compartment of the shell (in order to release the medical device).

Further, according to an embodiment of the device according to the present invention, in said first position of the operating member, the first and the second part of the shell are maintained by the operating member in said locked configuration, and wherein upon rotation of the operating member into said second position, the operating member transforms the locked configuration into said unlocked configuration of the first and the second part of the shell (e.g. by moving the first part along the longitudinal axis with respect to the second part which disengages the latching members, e.g. hooks).

Further, according to an embodiment of the device according to the present invention, the protrusion of the operating member comprises a free end, wherein said free end butts against a stop formed on the first part of the shell when the operating member is arranged in its first position, so as to prevent a movement of the first part of the shell with respect to the second part of the shell along the longitudinal axis which maintains the first and the second part of the shell in said locked configuration, and wherein said free end of the protrusion is configured to disengage with the stop of the first part of the shell when the operating member is rotated from its first position into its second position. Further, particularly, the operating member is configured to displace the first part along the longitudinal axis with respect to the second part of the shell when the operating member is rotated from its first position into its second position so that the locked configuration is transformed into the unlocked configuration of the first and the second part of the shell.

For this, particularly, the operating member comprises a central rod member protruding from the knob of the operating member into the longitudinal recess along the longitudinal axis, wherein the rod member comprises an end section that forms a latch which engages with an aperture formed into the first part of the shell, such that the rod member pulls the first part of the shell along the longitudinal axis with respect to the second part of the shell so that the locked configuration of the first and the second part is transformed into said unlocked configuration.

Further, another aspect of the present invention relates to a system comprising an implantation tool according to one of the preceding claims and a medical device (to be implanted by the implantation tool), wherein the medical device is arranged in said compartment of the shell of the implantation tool. Particularly, said medical device is an implantable cardiac monitoring device.

Furthermore, yet another aspect of the present invention relates to a method for implanting a medical device using an implantation tool according to the present invention, comprising the steps of:
- providing the implantation tool, wherein said medical implant is arranged in the compartment of the shell,
- making an incision in the skin of the patient (at the implantation site),
- inserting the shell of the implantation tool through said incision into the tissue of the patient, thereby defining a pocket in said tissue under the skin for insertion of the medical implant,
- opening the shell for releasing the medical implant,
- retracting the core and holding the rod in fixed position and thereby sliding the rod into the compartment for maintaining the contact with the medical implant such that the medical implant is kept in one position in relation to the longitudinal axis, wherein the shell is retracted from the pocket such that the medical implant is arranged in said pocket.

Particularly, according to an embodiment of the method according to the present invention, before retracting the core, said operating member is rotated from the first into the second position such that the grip member is unlocked from the core and such that the first and the second part of the shell are brought into said unlocked configuration, in which the first and the second part can be moved/deflected apart from each other and the shell opens at the slots for releasing the medical device from the compartment of the shell.

Furthermore, according to yet another embodiment of the method according to the present invention, the step of retracting said core comprises holding the unlocked grip member in place, retracting the core by sliding the core inside the grip member such that said knob of the operating member moves away from the grip member thereby sliding the rod into the compartment such that the medical implant upon being released out of the compartment of the shell moves/deflects said first and second part of the shell apart such that the shell opens at the slots and the medical implant is released out of the compartment of the shell into said pocket.

Due to the present invention, a medical device, particularly an implantable cardiac monitoring device, can be implanted using only a relatively small number of steps (particularly, five steps, namely: 1. Make incision, 2. Insert shell to define pocket, 3. Rotate knob to unlock grip member and shell, 4. Retract tool, leaving medical device (implant) in pocket, 5. Close wound) such that the procedure is safe, easy to reproduce, and minimizes discomfort of the patient.

Other features which are considered as characteristic for the invention are set forth in the appended claims.

Although the invention is illustrated and described herein as embodied in a tool and method for subcutaneous device insertion, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 1A-1C show the individual components of an implantation tool according to one embodiment.

FIGS. 2A and 2B show a lateral view of the shell of the implantation tool according to FIGS. 1A-1C, which shell comprises a first (top) part and a second (bottom) part which can be locked to one another via latching members (e.g. hooks).

FIGS. 2D and 2E show a perspective view of the two parts of the shell according to FIG. 2C.

FIG. 8 shows a perspective view of an implantation tool with another grip member.

In the figures, like reference numerals are used for like components.

DETAILED DESCRIPTION OF THE INVENTION

Figure 4:
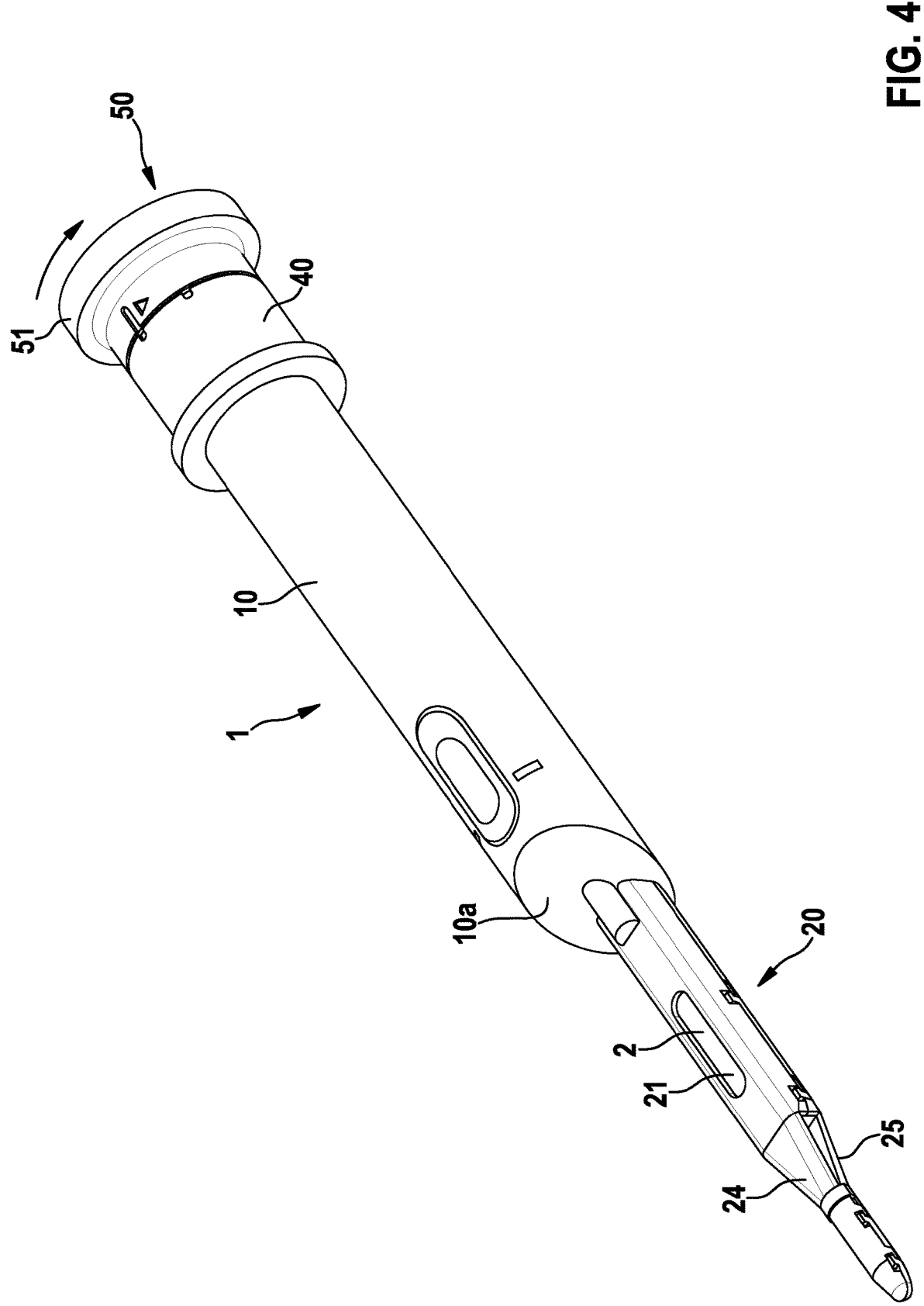
FIG. 4 shows a perspective view of the implantation tool shown in FIGS. 1A-1D, FIGS. 2A, 2B and FIGS. 3A, 3B in a locked state.

Referring now to the figures of the drawing in detail and first, particularly, to FIGS. 1A-1C thereof, there are shown the basic components of an exemplary embodiment of an implantation tool 1 for implanting a medical device 2 subcutaneously according to the present invention. As indicated in FIGS. 1A-1C, the implantation tool 1 comprises an elongated (e.g. tubular) core 10 (may also be called a handle) extending along a longitudinal axis L. The core 10 is formed with a longitudinal recess 11 extending along said longitudinal axis L in the handle 10. A shell 20, forming a tunneler, protrudes from a first end 10*a* of the core 10 in the direction of the longitudinal axis L (i.e. it is aligned with the core 10). The shell 20 further defines a compartment 21 for carrying/accommodating the medical implant 2 (FIG. 4, et seq.). The compartment 21 is connected to the longitudinal recess 11.

According to an embodiment of the device according to the present invention, for releasing the medical implant from the shell, the core is configured to be moved relative to said rod along the longitudinal axis, whereby the rod slides into said compartment for maintaining contact with the medical implant, whereby the medical implant is kept in one position in relation to the longitudinal axis by said rod, and whereby the medical implant is released from the compartment of the shell (and is thereby arranged in said pocket).

The movement of the core relative to the rod leads to a gradual retraction of the shell away from the pocket and the incision, whereby the retraction of the shell gradually releases the medical implant. The medical implant remains in the pocket after being completely released or disengaged from the shell. After the shell is completely retracted from the incision, only the rod temporarily stays in contact with the medical implant until the complete implantation tool is being retracted.

Further, the shell 20 is formed with a first openable slot 22 and an opposing second openable slot 23 for releasing the medical implant 2 from the shell 20/compartment 21. Further, the implantation tool 1 also comprises a rod 30 extending along the longitudinal axis L, which rod 30 is arranged in said longitudinal recess 11, wherein for releasing the medical implant 2 from the shell 20, the core 10 is configured to be moved relative to said rod 30 along the longitudinal axis L, whereby the rod 30 slides into said compartment 21 for maintaining contact with the medical implant 2 with an (e.g. concave) end 30*a*, keeping the medical implant 2 in a fixed position relative to the longitudinal axis L. When the two slots 22, 23 open up, the medical implant 2 can be released from the compartment 21 of the shell 20 such that the shell 20 is retracted from the implantable device 2 using the core 10. The implantable device 2 can e.g. be released into a pocket in the patient's tissue that was generated beforehand using the shell 20.

As indicated in FIGS. 2A-2B (see also FIGS. 1A-1C and 6), the two slots 22, 23 separate the shell 20 into a first (top) part 24 and a second (bottom) part 25. As can be seen from FIGS. 1A-1C, the first part 24 of the shell 20 may be formed with a window 28 into the compartment through which the medical implant 2 can be inspected (cf., e.g., FIG. 4).

Particularly, the first part 24 of the shell 20 is configured to be moved along the longitudinal axis L (away from the tip of the shell 20 as indicated by the arrow in the lower part of FIGS. 2A-2B) with respect to the second part 25 of the shell 20 to transform a locked configuration of said two parts 24, 25 of the shell 20, in which the two parts 24, 25 of the shell 20 cannot be moved/deflected away from each other and said slots 22, 23 remain closed (cf. upper part of FIGS. 2A-2B), into an unlocked configuration of said two parts 24, 25 of the shell 20, in which unlocked configuration the two parts 24, 25 of the shell 20 can be moved/deflected away from each other so as to open the compartment 21 at the slots 22, 23 for releasing the medical implant from the shell 20 (cf. lower part of FIGS. 2A-2B).

Particularly, as shown in FIGS. 2A-2B, at each of said slots 22, 23 (FIGS. 2A-2B only show slot 23) the first part 24 and the second part 25 of the shell 20 each comprise at least one latching member 26, 27, particularly in the form of a hook, wherein each latching member 26 of the first part 24 of the shell 20 engages with an associated latching member 27 of the second part 25 of the shell 20 when the first and the second part 24, 25 of the shell 20 reside in said locked configuration (cf. upper part of FIGS. 2A-2B), and wherein the latching members 26 of the first part 24 of the shell 20 are disengaged from the latching members 27 of the second part 25 of the shell 20 when the first and the second part 24, 25 of the shell 20 reside in said unlocked configuration (cf. lower part of FIGS. 2A-2B).

Figure 5:
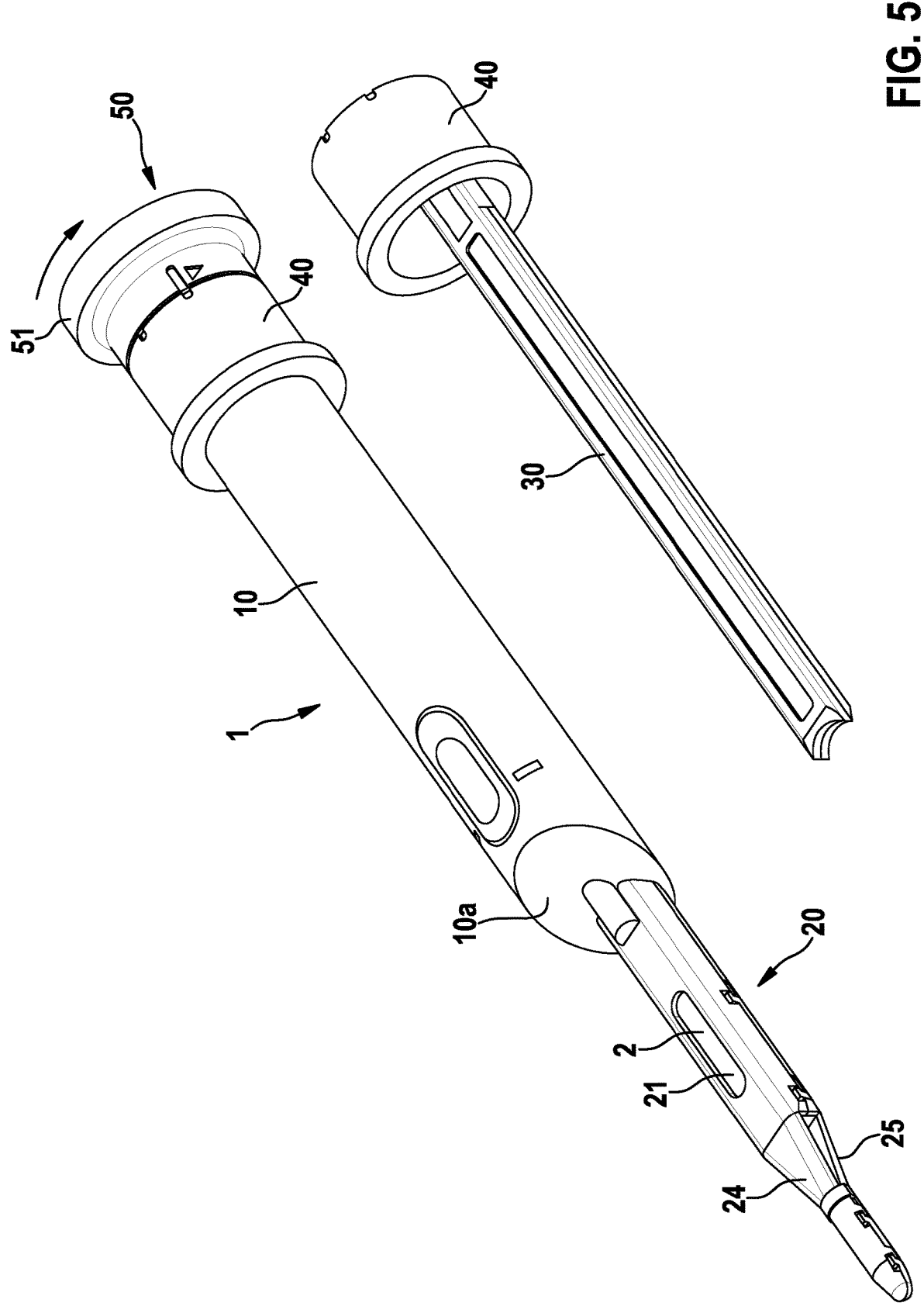
FIG. 5 shows a perspective view of the implantation tool and the rod and grip member shown in FIGS. 1A-1D, FIGS. 2A, 2B, FIGS. 3A, 3B and FIG. 4 in an unlocked state (i.e. grip member unlocked and first and second part of shell comprising unlocked configuration).
Figure 6:
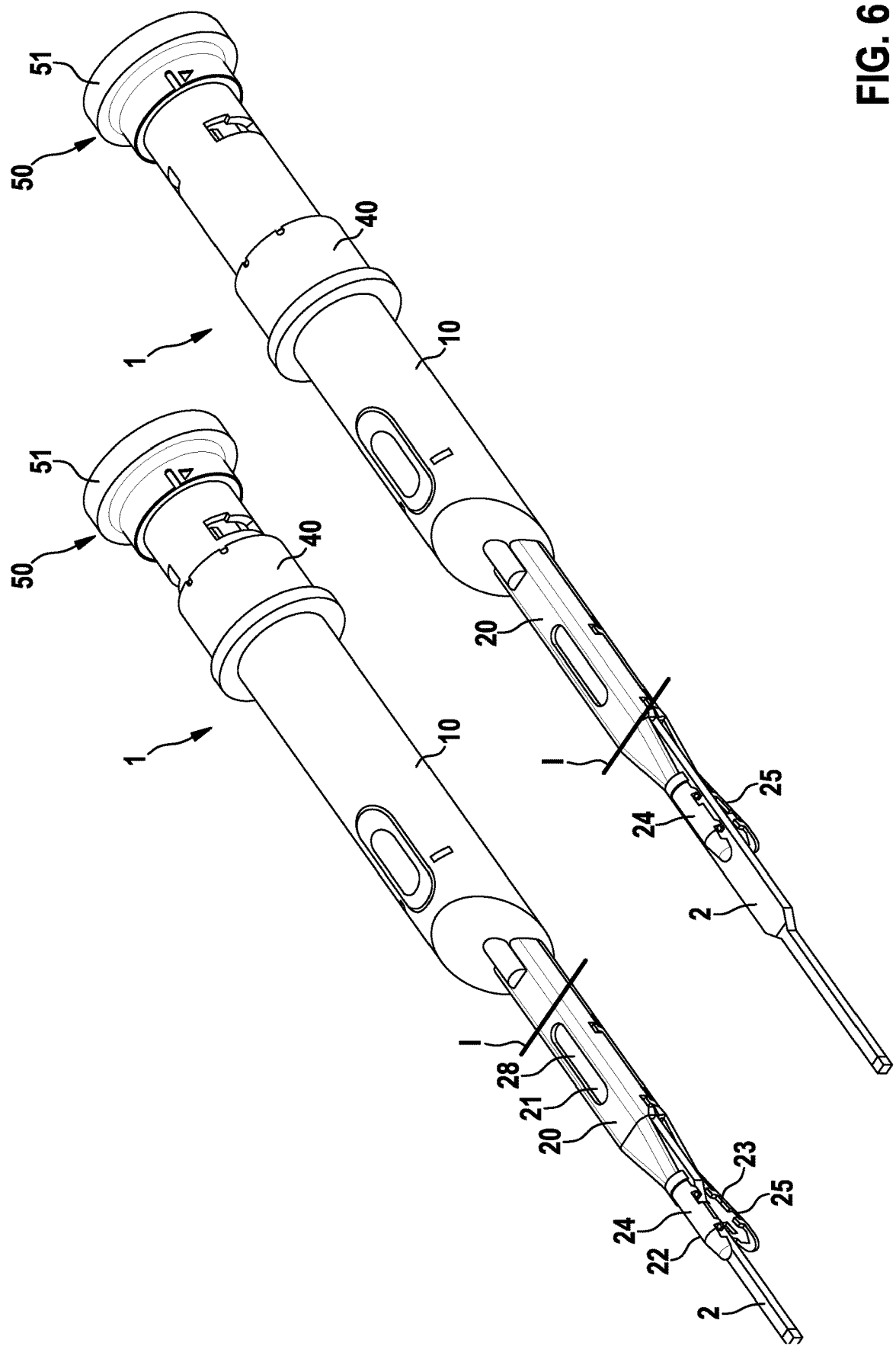
FIG. 6 shows illustrations of the installation tool upon release of the medical implant.

Further, as indicated in FIGS. 1A-1C and 5, the rod 30 of the implantation tool 1 is connected to a grip member 40 (may also be called ring member), which grip member 40 encompasses the core 10, so that the grip member 40 can be held fixed (e.g. by a hand of the user of the tool) and the core 10 can slide in the grip member 40 for sliding the rod 30 into said compartment 21 of the shell 20. The movement of the core 10 that causes rod 30 to enter the compartment 21 such that the shell is retracted from the medical implant 2 out of the compartment 21 is a retracting movement upon which the operating member 50 mounted at a second end 10*b* (opposite to the first end 10*a*) of core 10 becomes spaced apart from the grip member 40 as indicated in FIG. 6. Here, the incision in the skin of the patient is referenced with "I", through which the shell 20 is inserted into the tissue of the patient in order to generate a pocket for accommodating the medical device/implant 2. As can be seen from FIG. 6, upon retracting the core 10, the rod 30 actually keeps the medical implant 2 positioned in the pocket, i.e., at the implantation site, while the implant 2 is released from the compartment 21 of the shell 20 due to the retracting of the core 10 in a way that the medical implant 2 is kept in one position in relation to the longitudinal axis L by said rod 30, wherein the shell 20 is configured to be retracted from the medical implant 2.

The operating member 50 is rotatable and mounted to the second end 10*b* of the core 10 opposite the shell 20, and is configured to be rotated from an initial first position into a second position. The operating member 50 serves for unlocking the grip member 40 so that the core 10 can slide in the grip member 40, i.e., can be retracted with respect to the grip member 40, and for retracting the first (top) part 24 of the shell 20 with respect to the second (bottom) part 25 of the shell 20, so that the latching members 26, 27 get out of engagement (corresponding to the unlocked configuration of the shell 20 where the rod 30 contacts the implant 2 and keeps the medical implant 2 in a position. The two parts of the shell 20 open up/pivot away from each other resulting in enlarged slots 22, 23 through which the implant 2 can be slid out of the compartment 21 by being kept in position by the rod 30 (and the retracting movement of the core), cf. for instance right hand side of FIG. 6. Further, FIGS. 4 and 5 show rotation of the operating member 50 via knob 51 from the first position (cf. FIG. 4) to the second position (cf. FIG. 5).

Figure 1D:
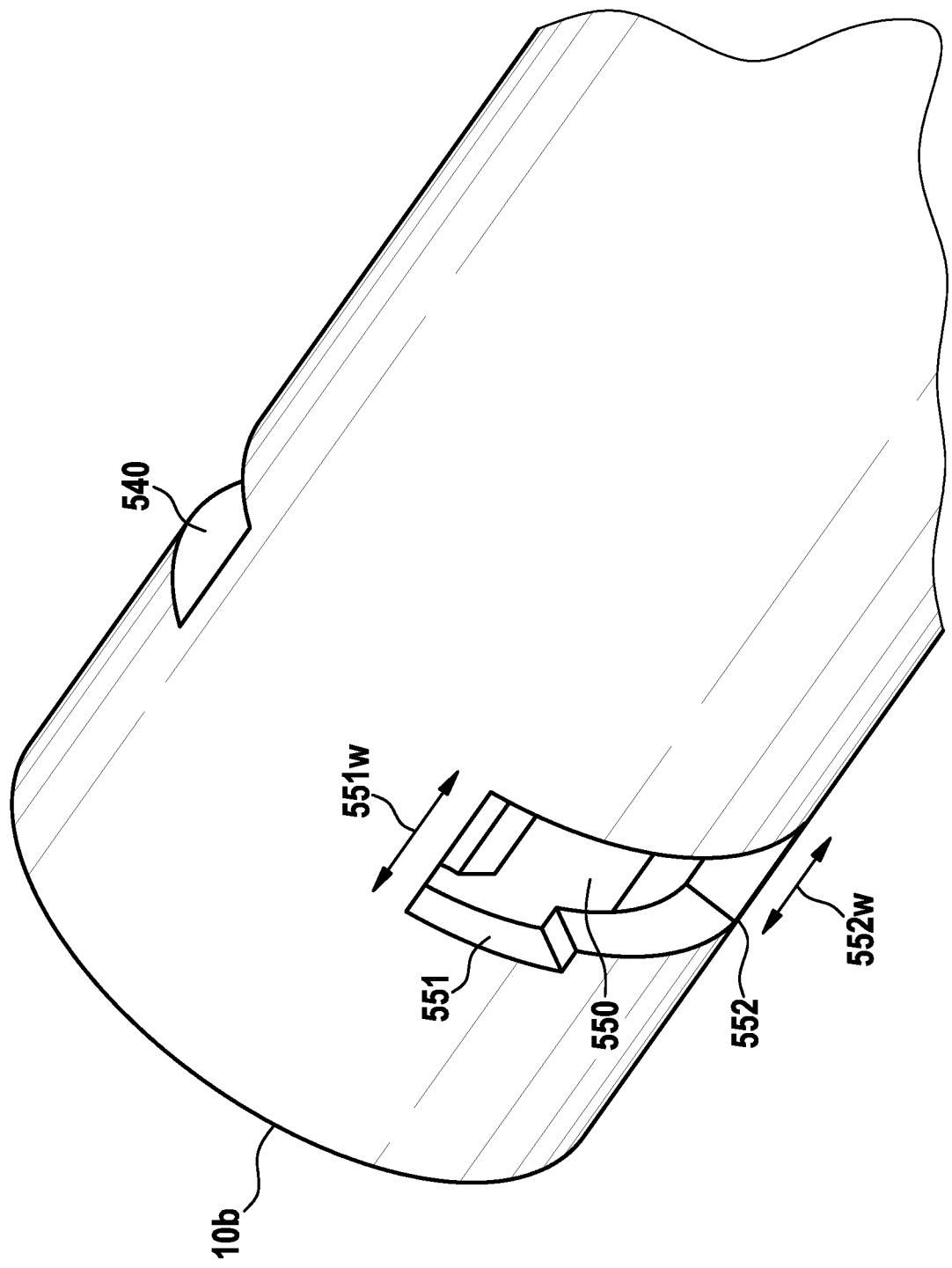
FIG. 1D shows one end of the core of the implantation tool according to FIGS. 1A-1C.
Figure 2C:
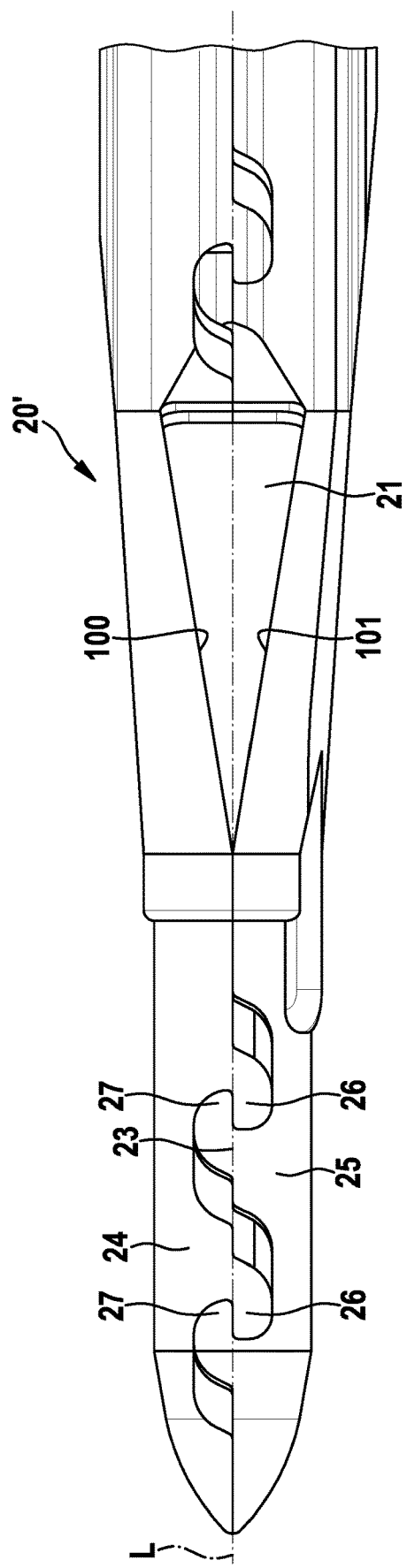
FIG. 2C shows a lateral view of another shell of the implantation tool which is compatible with the implantation tool of FIGS. 1A-1C.

Another shell 20' is shown in FIG. 2C. The shell 20' is compatible with the implantation tool shown in FIG. 1 and all other embodiments disclosed herein. Compared to the shell 20 shown in FIGS. 2A-2B, the latches 26, 27 have an increased unlocking distance to improve clearance after an unlock operation. Also, the second row (on the right hand) of latches 26, 27 is moved forwards to the tip to reduce nose opening during deposition of the implant 2. The necks 100, 101 have a reduced taper to create a smooth transition when shoulders of the implant 2 enter the other shell 20'.

A perspective view of the other shell 20' of FIG. 2C is shown in FIGS. 2D-2E. On an inner side (facing the compartment 21) of the first part 24 a first ramp 102 is formed. In an analogue manner, a second ramp 103 is formed on an inner side (facing the compartment 21) of the second part 25. After the other shell is unlocked, the ramps 102, 103, which contact the implant 2, separate the first part 24 and the second part 25, thus opening the other shell 20' for implant 2 extraction.

Figure 3B:
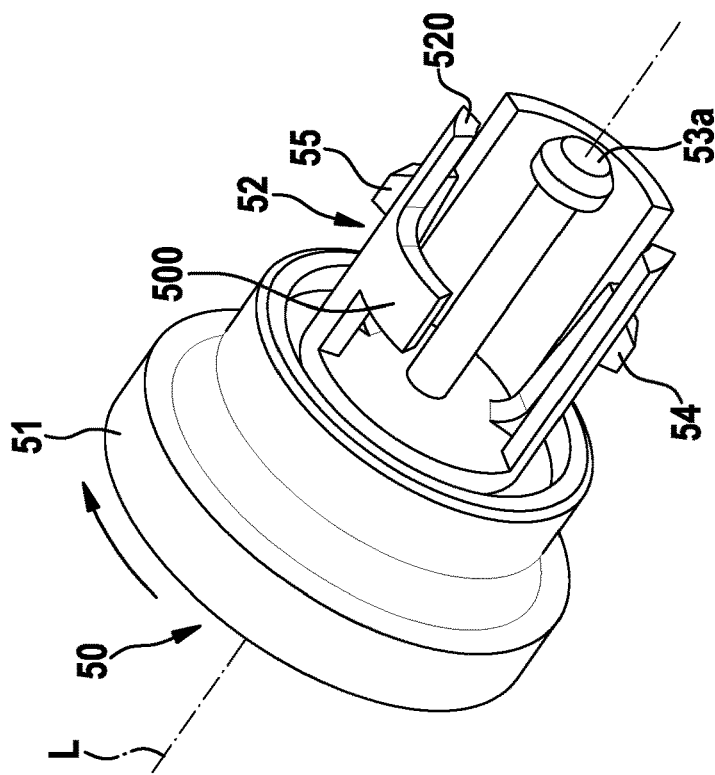
FIGS. 3A and 3B show a perspective view of the operating member of the tool according to FIGS. 1A-1C and FIGS. 2A and 2B.
Figure 3A:
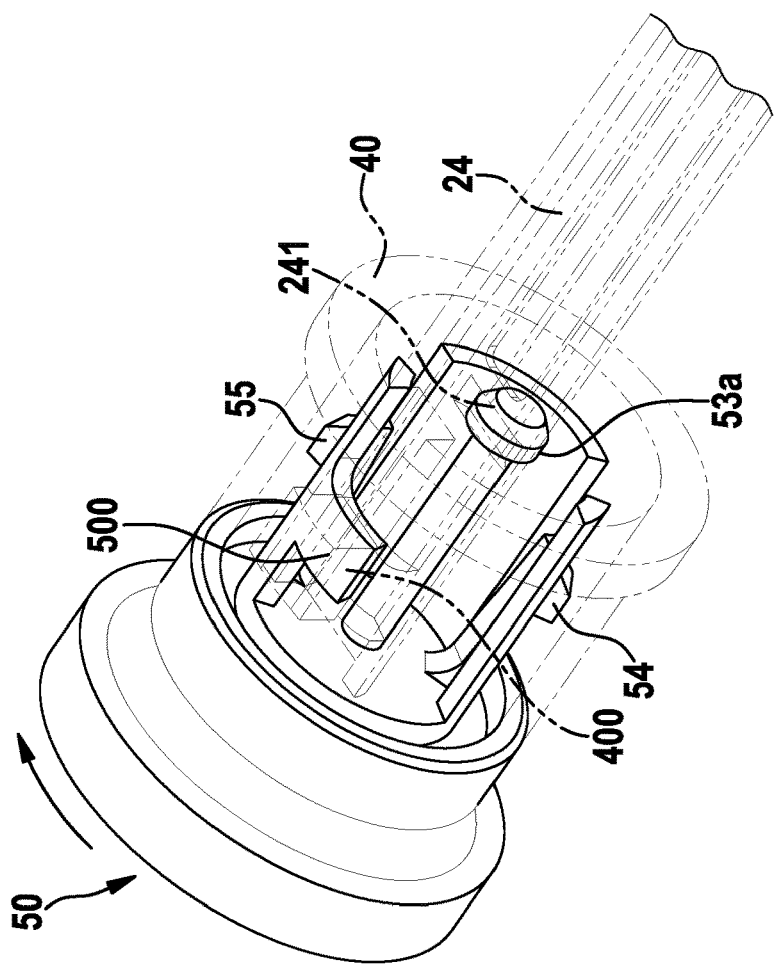

An exemplary mechanism for unlocking the grip member 40 and for bringing the shell 20 to its unlocked configuration is shown in FIGS. 3A-3B. According thereto, the operating member 50 comprises a knob 51 arranged outside said longitudinal recess 11 of the core 10, from which knob 51 a protrusion 52 of the operating member 50 protrudes along the longitudinal axis L (cf. right hand side of FIGS. 3A-3B), which protrusion 52 is arranged in said longitudinal recess 11.

The operating member 50 comprises a pin 500 which protrudes in a circumferential direction of the core 10 from said protrusion 52, wherein said pin 500 engages with a slot 400 formed in the grip member 40 (cf. left hand side of FIG. 3) when the grip member 40 is arranged adjacent the operating member 50 and the operating member 50 is arranged in its first position. This locks the grip member 40 with respect to the core 10 and prevents an axial movement of the grip member 40 with respect to the core 10. Further, once the operating member 50 has been rotated into its second position, the pin 500 disengages with the slot 400 and the grip member 40 is free to move axially with respect to the core 10.

Furthermore, the protrusion 52 of the operating member 50 comprises a free end 520 (cf. e.g. the right hand side of FIGS. 3A-3B), wherein said free end 520 butts against a stop 240 (cf. also FIGS. 1A-1C) formed on the first part 24 of the shell 20 when the operating member 50 is arranged in its first position, so as to prevent a movement of the first part 24 of the shell 20 with respect to the second part 25 of the shell 20 along the longitudinal direction L which prevented movement maintains the first and the second part 24, 25 of the shell 20 in their locked configuration. Furthermore, said free end 520 is configured to disengage with the stop 240 when the operating member 50 is rotated from its first position into its second position, so that then a small axial movement of the first part 24 of the shell 20 with respect to the second part 25 of the shell is allowed as indicated in FIGS. 2A-2B (lower part). This axial movement is generated with help of a rod member 53 of the operating member 50, which rod member 53 protrudes from the knob 51 of the operating member 50 into the longitudinal recess 11 along the longitudinal axis L. The rod member 53 (cf. FIG. 3 right hand side) comprises an end section 53a that forms a latch which engages with an aperture 241 formed in the first part 24 of the shell (cf. FIGS. 1A-1C), such that the rod member 53 pulls the first part 24 of the shell 20 along the longitudinal axis L with respect to the second part 25 of the shell 20 when the operating member 50 is rotated from its first position into its second position (by acting on the knob 51 accordingly) which results in the unlocked configuration of the shell 20 shown in the lower part of FIGS. 2A-2B.

The rotational movement of the operating member 50 from the first position towards the second position with respect to the core 10 can be guided by two latches 54, 55 which protrude from the knob 51 along the longitudinal axis L and slidingly engage with corresponding slots 540, 550 arranged in the core 10.

According to an embodiment, the second end 10b of the core 10 as depicted in FIG. 1D may be implemented. The slots 540, 550 have a shape comprising a short leg 551 and a long leg 552, both having a width, wherein the width 551w of the short leg 551 is wider than the width 552w of the long leg 552. In the locked configuration of the shell 20, latches 54, 55 (cf. FIGS. 3A-3B right hand side) are engaged with the long leg 552 of the slots 540, 550. Due to the assigned width of the long leg 552 and the engagement of the latches 54, 55 a movement of the operation member 50 along the longitudinal direction L is not possible. In the unlocked position of the shell 20, the latches 54, 55 are engaged with the short leg 551 of the slots 540, 550. When operation member 50 (cf. FIGS. 3A-3B) is moved from the first position towards the second position with respect to the core 10, the latches 54, 55 are moved from a position engaged with the long leg 552 to a position engaged with the short leg 551. In this position operation member 50 is movable in longitudinal direction L about the difference in width between the short leg 551 and the long leg 552. This short movement is transferred to the first part 24 of the shell 20 by the end section 53a of the rod member 53, which is engaged with the aperture 241 of the first part 24, and causes the disengagement of the latches 26 and 27 by relative motion of the latching members 26, 27.

The shape of the slots in the core 540, 550 define the length of relative motion for the actual unlocking of the latching members 26, 27. Preferably, in the unlocked position of the shell 20, the latch 55 is aligned with the short leg 551 along the longitudinal axis. The same applies to latch 54 and short leg of slot 540 (not shown in FIG. 1D). The width 551w of the short leg 551 is what allows the two parts 24, 25 of the shell 20 to move slightly relative to each other to unlock, before they begin to be pulled back together by operation member 50 as the latches 54, 55 fully engage with the core. The relative motion is taken along the longitudinal axis to unlatch the latching members 26, 27, therefore, it is the width 551w of the short leg 551 that defines the amount of relative motion for operation member 50 which is necessary for bringing shell 20 from the locked into the unlocked position.

Figure 3C:
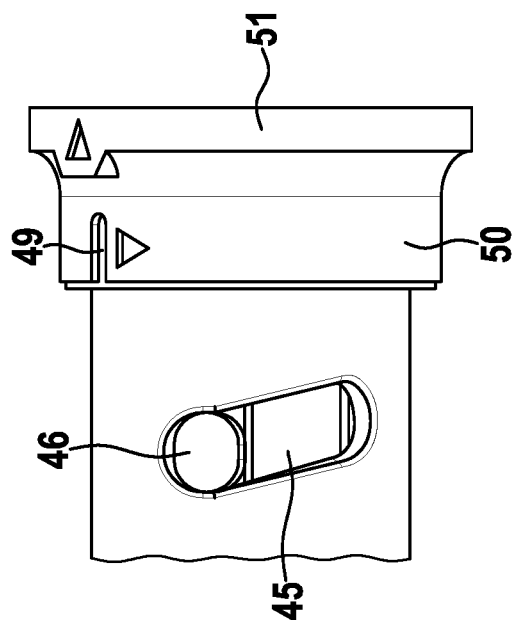
FIGS. 3C-3E show a lateral view of another embodiment of the operating member which is compatible with the implantation tool according to FIGS. 1A-1C.
Figure 3E:
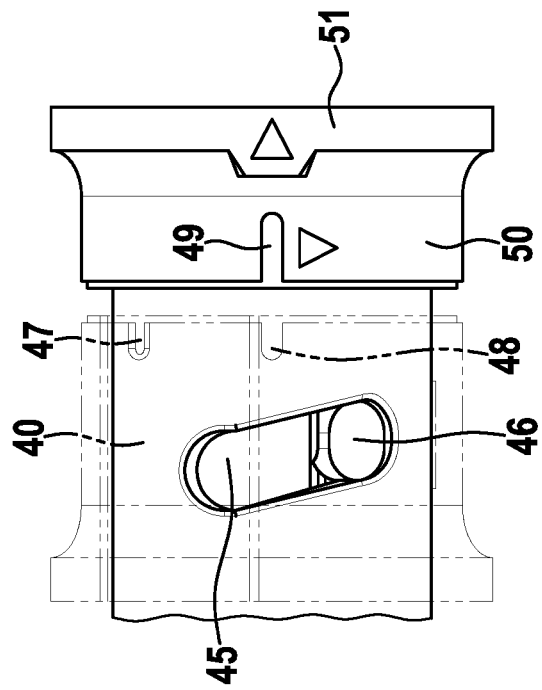
Figure 3D:
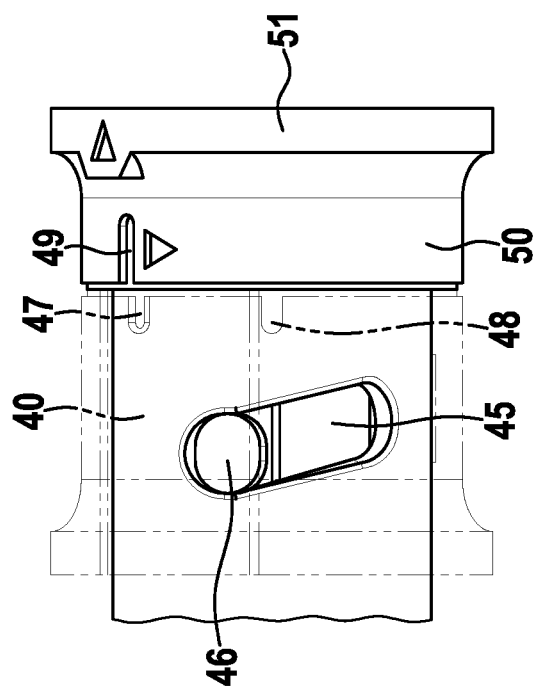

Another unlocking mechanism is shown in FIGS. 3C-3E. The core 10 comprises a cam 46 which is arranged in a slot 45 (instead of the latches 54, 55 as shown in FIGS. 3A-3B). This leads to less friction and allows a smoother operation of the grip member 40. The core may comprise more than one cam 46, for example, two cams may be provided (not shown). Two cams may be arranged on opposite sides of the core 10. The grip member 40 has two markers, a first marker 47 and a second marker 48. The operating member 50 has a marker 49. In the locked position (lower left side of FIGS. 3C-3E), the first marker 47 of the grip member 40 is aligned with the marker 49 of the operating member 50. In this position, the grip member 40 is in contact with the operating member 50. By rotating the operating member 50, the cam 46 follows the slot 45. Because the slot 45 is angled, the operating member 50 therefore pulls the top side 24 of the shell 20 proximally as the operating member 50 is rotated. Hereby, the latches are unlocked (not shown) and the implantation tool is in an unlocked position (lower right side of FIG. 3a). In the unlocked position, the grip member 40 is separated by a distance from the operating member 50. The transition from the locked position into the unlocked position occurs by a single step procedure. The implantation tool can be configured to generate a sound when reaching the locked position or the unlocked position, respectively. The sound may be generated by a small bump on the inner surface of the slot 45 (not shown). The cam 46 makes a slight clicking sound as it passes over the bump.

Figure 7:
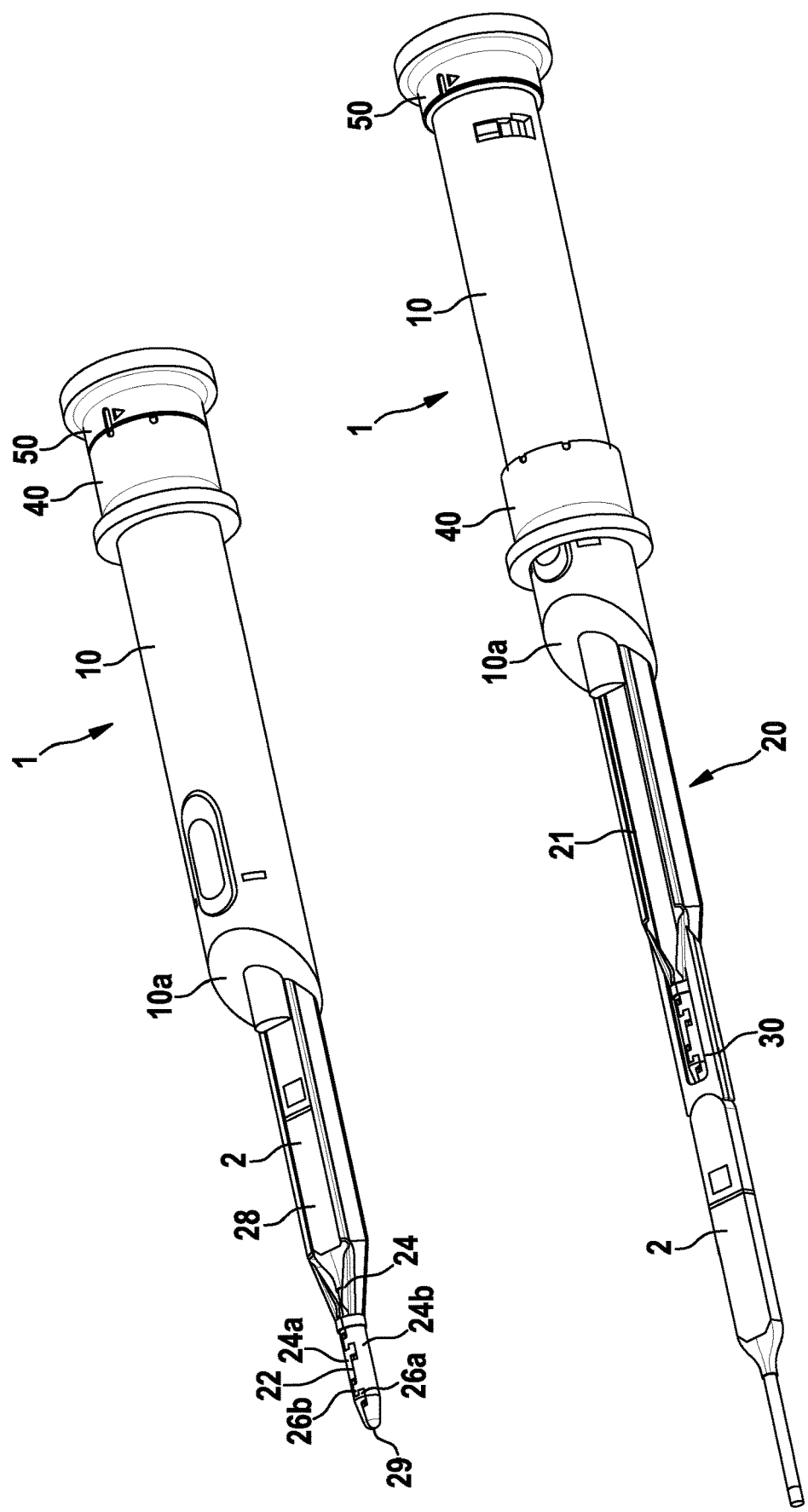
FIG. 7 shows perspective views of a further embodiment of an implantation tool.
Figure 9A:
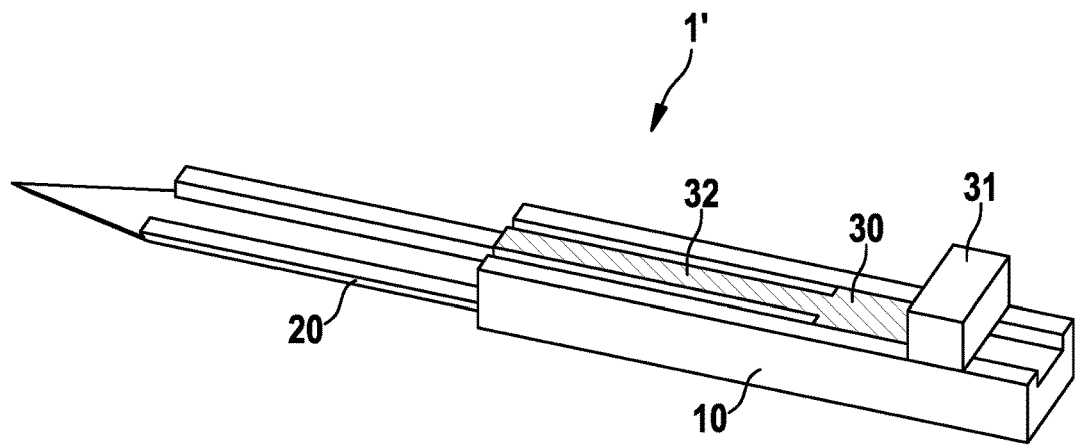
FIG. 9 shows yet another implantation tool when used to implant a medical device.
Figure 9B:
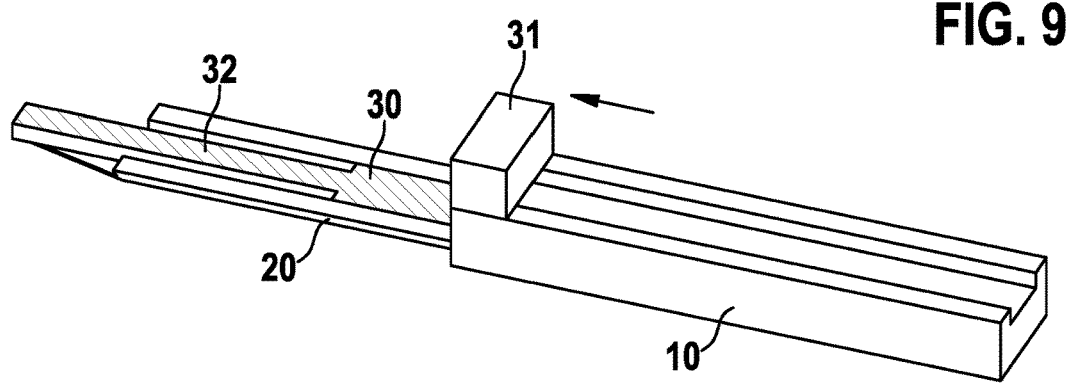
Figure 9C:
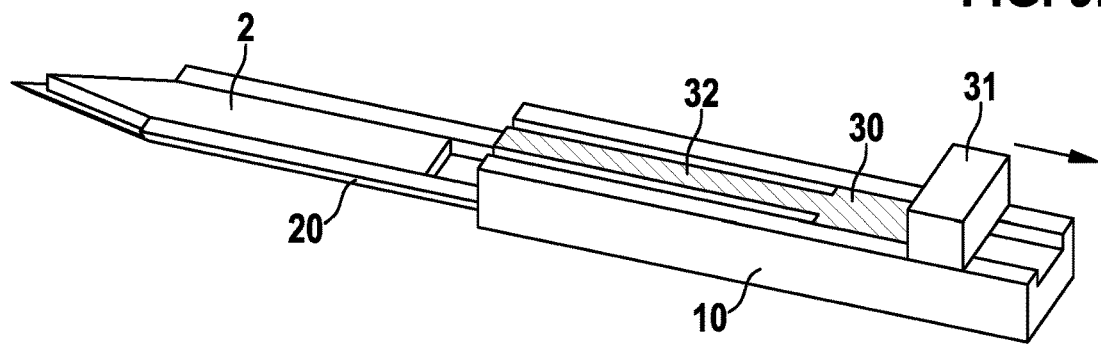
Figure 9D:
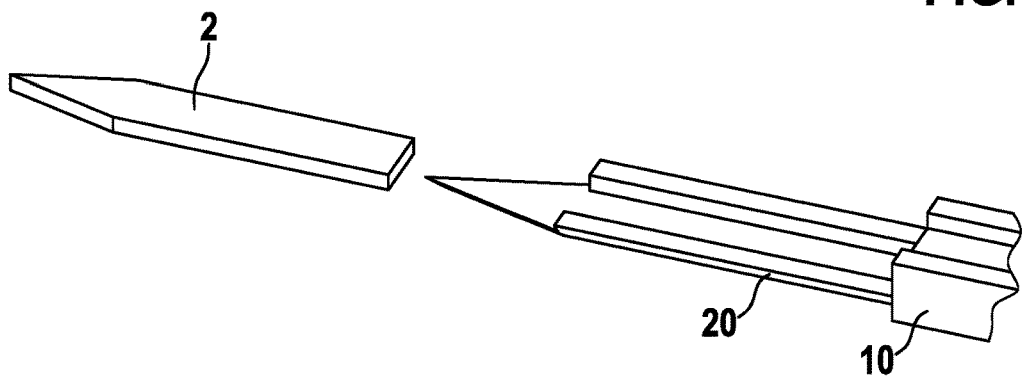

Further, instead of having two slots 22, 23 which allow the shell 20 to open from top to bottom, the shell 20 may also merely comprise a single slot 22 arranged on a top side 24 of the shell 20 as shown in FIG. 7. Here, said single slot 22 extends from a window 28 of the shell 20 that is formed into the top side 24 of the shell 20 towards a tip 29 of the shell 20, wherein the medical implant 2 is visible through said window 28 when the medical implant 2 is arranged in the compartment 21 defined by the shell 20.

Particularly, as can be inferred from FIG. 7, the slot 22 divides a section of said top side 24 of the shell 20 into a first and a second part 24a, 24b, wherein at said slot 22 the first part 24a and the second part 24b each comprise at least one latching member 26a, 26b, wherein each latching member 26a of the first part 24a of the shell 20 engages with an associated latching member 26b of the second part 24b of the shell 20 when the first and the second part 24a, 24b of the shell 20 reside in a locked configuration, in which the two parts 24a, 24b of the shell 20 cannot be deflected from each other and said at least one slot 22 remains closed. Furthermore, the latching members 26a of the first part 24a of the shell 20 are disengaged from the latching members 26b of the second part 24b of the shell 20 when the first and the second part 24a, 24b of the shell 20 reside in said unlocked configuration, in which the two parts 24a, 24b of the shell 20 can be moved/deflected away from each other so as to open the single slot 22 for releasing the medical implant 2 from the shell 20.

Also here, by way of sliding the rod 30 into the compartment 21 (e.g. by holding grip member 40 fixed and retracting the core 10) the medical implant 2 can be released from the compartment 21 with the rod 30 through the opened slot 22 in a way that the medical implant 2 is kept in one position in relation to the longitudinal axis L by said rod 30, wherein the shell is configured to be retracted from the medical implant 2 in order to arrange the implant 2 in the tissue pocket created before.

The individual steps of implantation of the medical device 2 using the implantation tool 2 can for instance be inferred from FIG. 6. According thereto, an implantation tool 1 according to the invention is provided, wherein said medical implant 2 is arranged in the compartment 21 of the shell 20. Further, an incision is made in the skin of the patient as marked in FIG. 6 with the reference symbol I. Thereafter, the shell 20 of the implantation tool 1 is inserted through said incision I into the tissue of the patient and a pocket in said tissue under the skin of the patient is formed for insertion of the medical implant 2. Then, the core 10 is retracted (FIG. 6 shows retracting the core 10) and thereby the rod 30 is slid into the compartment 21 such that the medical implant 2 is released from the shell 20 and is arranged in said pocket.

Particularly, according to an embodiment of the method according to the present invention, before retracting the core 10, said operating member 50 (see also above) is rotated from its first position into its second position such that the grip member 40 is unlocked from the core 10 and such that the first and the second part 24, 25 of the shell 20 are brought into said unlocked configuration, in which the first and the second part 24, 25 can be moved/deflected apart from each other and the compartment 21 opens at the slots 22, 23 for releasing the medical device 2.

According to yet another embodiment of the method according to the present invention, the step of retracting said core 10 comprises holding the unlocked grip member 40 in place, retracting the core 10 by sliding the core 10 inside the grip member 40 such that said knob 51 of the operating member 50 moves away from the grip member 40 thereby sliding the rod 30 into the compartment 21 of the shell 20 such that the medical implant 2 upon being released from the compartment 21 of the shell 20 moves/deflects said first and second part 24, 25 of the shell 20 apart such that the shell 20 opens at the slots 22, 23 and the medical implant 2 is released out of the compartment 21 of the shell 20 into said pocket. Thus actually only five steps are needed for implantation of the medical device 2:

Make incision I;
Insert shell 20 to define pocket;
Rotate knob 51 to unlock grip member 40 and shell 20;
Retract tool 1, leaving medical device (implant) 2 in created pocket;
Close wound.

This makes the method robust and comfortable for the patient at the same time.

Another embodiment of a grip member 40' is shown in FIG. 8. The grip member 40' extends from the first end 10a of the core 10 to the operating member 50. Thus, is covers the complete length of the core 10. Besides the outer appearance, the other components of the grip member 40' are the same as in the grip member 40 described above, in particular the rod 30 is arranged in the grip member 40'.

Finally, FIG. 9 shows an alternative variant of the implantation tool 1'.

Here, the tool 1' comprises a tunneler 20, and a rod 30 having a slider 31 for moving the medical implant 2 out of a compartment in the core 10 onto the tunneler 20. Further rod 30 having a protection extension 32, which extends distally from the rod and has a length suitable to cover the medical implant 2 so that the medical implant 2 is then arranged between the tunneler 20 and the protection extension 32 which therefore covers the implant 2 from above. The protection extension 32 does not only protect the medical implant from being damaged or scratched, it also protects the flexible part of the medical implant 2 from moving upward during the injection of the medical implant 2 out of the compartment in the core 10. In one embodiment the protection extension 32 also protect the distal tip of the medical implant 2 by a protector tip situated distally of the distal tip of the medical implant 2, wherein the protector tip is bended down in direction to the tunneler 20 in order to distally surround the distal tip of the medical implant 2.

Also here, at first, an incision is made.

Then the tunneler 20 is inserted into the tissue to form a pocket for receiving the implant 2 (A).

Then, the rod 30 is advanced by advancing the slider 31 to inject the implant 2 protected by the protection extension 32 into the pocket (B), wherein the implant 2 gets positioned on top of the tunneler 20.

Then, the slider 31 and therewith rod 30 and the protection extension 32 is withdrawn (C) and afterwards the tool 1 is withdrawn (D), leaving the implant 2 in the created pocket.

Finally the wound is closed.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein.

Therefore, it is the intent to cover all such modifications and alternate embodiments as may come within the true scope of this invention.

The invention claimed is:

1. An implantation tool for implanting a medical implant subcutaneously, the implantation tool comprising:
   a core extending along a longitudinal axis, said core being formed with a longitudinal recess extending along said longitudinal axis;
   a shell protruding from an end of said core in a direction of said longitudinal axis, said shell defining being a structure separate from, and movable relative to said core, said shell being formed with a compartment, and said compartment being fluidly connected to said longitudinal recess, for carrying the medical implant, and said shell having a first part and a second part encasing the medical implant therebetween in a locked configuration of said shell and being configured to move apart in a transverse direction relative to the longitudinal direction to assume an unlocked configuration for releasing the medical implant from said shell; and
   a rod extending along the longitudinal axis and arranged in said longitudinal recess and movably mounted relative to said longitudinal recess such that said rod remains in contact with the medical implant when the medical implant is disposed in said shell and while said shell with said first and second parts is withdrawn in the longitudinal direction to release the medical implant from said shell; and an operating member mounted to an end of said core opposite said shell, said operating member being rotatably configured about the longitudinal axis extending in the longitudinal direction from an initial first position into a second position, wherein said shell is in the unlocked configuration when said operating member is in the second position.

2. The implantation tool according to claim 1, wherein, for releasing the medical implant from said shell, said core is configured for movement relative to said rod along said longitudinal axis, wherein said rod slides into said compartment for maintaining the contact with the medical implant, wherein the medical implant is kept in one position by said rod, and wherein the medical implant is released from said compartment of said shell.

3. The implantation tool according to claim 1, wherein said shell is formed with a first slot.

4. The implantation tool according to claim 3, wherein said shell is formed with a second slot opposite said first slot.

5. The implantation tool according to claim 4, wherein said first and second slots are disposed to segment said shell into said first part and said second part.

6. The implantation tool according to claim 5, wherein said first part of said shell is configured for movement along said longitudinal axis with respect to said second part of said shell to transform the locked configuration of said two parts, in which said two parts cannot be deflected from each other and said slots remain closed, into the unlocked configuration of said two parts, in which said two parts are movable away from each other so as to open said compartment at said slots for releasing the medical implant from said shell.

7. The implantation tool according to claim 6, wherein each of said first and second parts of said shell are formed with a latching member at the respective said slot, wherein each latching member of said first part of said shell engages with an associated latching member of said second part of said shell when said first and second parts are in said locked configuration, and wherein said latching members of said first part of said shell are disengaged from said latching members of said second part of said shell when said first and second parts of said shell are in said unlocked configuration.

8. The implantation tool according to claim 1, wherein said shell is formed with a single slot on a top side of said shell, said single slot extending from a window formed into a top side of said shell towards a tip of said shell, and wherein the medical implant is visible through said window when the medical implant is disposed in said compartment defined by said shell.

9. The implantation tool according to claim 8, wherein:
   said slot divides a section of said top side of said shell into said first part and said second part;
   said first part and said second part each has at least one latching member at said slot;
   each latching member of said first part of said shell engages with an associated latching member of said second part of the shell when said first and second parts are in the locked configuration, in which said first and second parts cannot be deflected from each other and said slot remains closed; and
   said latching members of said first part are disengaged from said latching members of said second part of said shell, when said first and second parts of said shell are in the unlocked configuration, in which said first and second parts of said shell can be deflected away from each other so as to open said slot for releasing the medical implant from said shell.

10. The implantation tool according claim 1, wherein said rod is connected to a grip member that encompasses said core, and wherein said grip member can be held fixed and said core can slide in said grip member for sliding said rod into said compartment of said shell.

11. The implantation tool according to claim 1, wherein said operating member is formed with a knob arranged outside said longitudinal recess, wherein a protrusion of said operating member protrudes from said knob along the longitudinal axis, and wherein said protrusion is arranged in said longitudinal recess of said core.

12. The implantation tool according to claim 11, further comprising a grip member, wherein in a first position of said operating member said grip member is locked by said operating member when said grip member is arranged adjacent said operating member, so that said rod is movable with respect to said core, and wherein in a second position of said operating member said grip member is unlocked with respect to said core so that said core is slideable in said grip member for sliding said rod into said compartment of said shell.

13. The implantation tool according to claim 11, wherein said operating member comprises a pin protruding in a circumferential direction of core from said protrusion, wherein said pin engages with a slot formed in said a grip member, when said grip member is arranged adjacent said operating member and said operating member is arranged in its first position, and wherein said pin disengages with said slot of said grip member when said operating member is rotated into the second position so that said grip member is unlocked with respect to said core and said core is slideable in said grip member for sliding said rod into said compartment of said shell.

14. The implantation tool according to claim 11, wherein, in a first position of said operating member, said first and second parts of said shell are maintained by said operating member in the locked configuration, and wherein, upon rotation of said operating member into the second position of said operating member, said operating member transforms the locked configuration into the unlocked configuration of said first and second parts of said shell.

15. The implantation tool according to claim 14, wherein the protrusion of said operating member comprises a free end, wherein said free end butts against a stop formed on a first part of said shell when said operating member is arranged in the first position, so as to prevent a movement of said first part of said shell with respect to said second part of said shell along the longitudinal direction so that the first and second parts of said shell are maintained in the locked configuration, and wherein said free end is configured to disengage from said stop when said operating member is rotated from the first position into a second position, and wherein said operating member is configured to displace said first part of said shell along said longitudinal axis with respect to said second part of said shell when said operating member is rotated from the first position into the second position so that the locked configuration is transformed into the unlocked configuration of said first and second parts of said shell.

16. The implantation tool according to claim 15, wherein said operating member comprises a rod member protruding from said knob of said operating member into said longitudinal recess along said longitudinal axis, wherein said rod member comprises an end section that forms a latch which engages with an aperture formed in said first part of said shell, such that said rod member pulls said first part of said shell along said longitudinal axis with respect to said second part of said shell when said operating member is rotated from the first position into the second position so that the locked configuration of said first and second parts of said shell is transformed into the unlocked configuration.

17. A system, comprising:
an implantation tool according to claim 1; and
a medical implant disposed in the compartment of the shell of said implantation tool.

18. A method for implanting a medical implant, comprising:
providing an implantation tool according to claim 1, the implantation tool having the medical implant arranged in the compartment of the shell;
making an incision in the skin of the patient;
inserting the shell of the implantation tool through the incision into the tissue of the patient, thereby defining a pocket in the tissue under the skin of the patient for insertion of the medical implant;
opening the shell for releasing the medical implant; and
retracting the core of the implantation tool and holding the rod in fixed position and thereby sliding the rod into the compartment for maintaining the contact with the medical implant such that the medical implant is kept in one position and the shell is retracted from the pocket such that the medical implant remains in the pocket.

* * * * *